US008974487B2

(12) United States Patent
Connor et al.

(10) Patent No.: US 8,974,487 B2
(45) Date of Patent: Mar. 10, 2015

(54) ANEURYSM OCCLUSION DEVICE (75) Inventors: Robert A. Connor, Minneapolis, MN (US); Muhammad Tariq Janjua, Inver Grove Heights, MN (US)

(73) Assignee: Aneuclose LLC, Forest Lake, MN (US)

( * ) Notice: Subject to any disclaimer, the term of this patent is extended or adjusted under 35 U.S.C. 154(b) by 85 days.

(21) Appl. No.: 12/989,048

(22) PCT Filed: Apr. 24, 2009

(86) PCT No.: PCT/US2009/002537
§ 371 (c)(1),
(2), (4) Date: Oct. 21, 2010

(87) PCT Pub. No.: WO2009/134337
PCT Pub. Date: Nov. 5, 2009

(65) Prior Publication Data
US 2011/0046658 A1    Feb. 24, 2011

Related U.S. Application Data (60) Provisional application No. 61/126,027, filed on May 1, 2008, provisional application No. 61/126,047, filed on May 1, 2008.

(51) Int. Cl.
*A61M 29/00* (2006.01)
*A61B 17/12* (2006.01)
*A61B 17/00* (2006.01)

(52) U.S. Cl.
CPC ..... *A61B 17/12022* (2013.01); *A61B 17/12172* (2013.01); *A61B 2017/12095* (2013.01); *A61B 2017/12054* (2013.01); *A61B 2017/00884* (2013.01); *A61B 17/1219* (2013.01); *A61B 17/12177* (2013.01); *A61B 17/12113* (2013.01)
USPC .......................................... 606/200; 606/198

(58) Field of Classification Search
CPC .................... A61B 17/12022; A61B 17/1219; A61B 17/12113; A61B 17/12186; A61B 17/12031; A61B 2017/12095; A61B 2017/00884; A61B 2017/12054; A61B 17/12177; A61B 17/12172
USPC ......... 606/194, 195, 198, 200, 127, 159, 191, 606/151; 604/8, 9; 600/37; 623/23.64, 623/23.68
See application file for complete search history.

(56) References Cited

U.S. PATENT DOCUMENTS 4,341,218 A * 7/1982 U ................................ 606/195
4,364,392 A   12/1982 Strother et al.
(Continued)

FOREIGN PATENT DOCUMENTS

CN    1717263 A       1/2006
JP    2000-512515 A   9/2000
(Continued)

OTHER PUBLICATIONS

"International Application Serial No. PCT/US2009/02537, Search Report mailed Jun. 17, 2009", 3 pgs.
(Continued)

*Primary Examiner* — Katrina Stransky (57) ABSTRACT

A device to treat an aneurysm can include a plurality of soft and compressible fill members. A flow conduit can carry the fill members in a liquid flow. A flexible, expandable, and liquid-permeable net or mesh enclosure can be inserted into and to fit within the aneurysm. The net or mesh enclosure can receive and retain the plurality of fill members while openings in the net or mesh enclosure allow enough liquid flow through the net or mesh enclosure to transport the fill members into the net or mesh enclosure. A resulting accumulation of the plurality of fill members within the net or mesh enclosure causes the net or mesh enclosure to expand and to come into contact with and generally conform with an interior wall of the aneurysm. This can substantially occlude the aneurysm and retain the net or mesh enclosure within the aneurysm.

30 Claims, 4 Drawing Sheets

(56) References Cited

U.S. PATENT DOCUMENTS

| | | | |
|---|---|---|---|
| 4,638,803 A * | 1/1987 | Rand | 606/192 |
| 5,041,090 A * | 8/1991 | Scheglov et al. | 604/101.02 |
| 5,334,210 A * | 8/1994 | Gianturco | 606/151 |
| 5,382,259 A | 1/1995 | Phelps et al. | |
| 5,522,822 A | 6/1996 | Phelps et al. | |
| 5,645,559 A | 7/1997 | Hachtman et al. | |
| 5,690,666 A * | 11/1997 | Berenstein et al. | 606/191 |
| 5,718,711 A | 2/1998 | Berenstein et al. | |
| 5,723,004 A | 3/1998 | Dereume et al. | |
| 5,749,894 A | 5/1998 | Engelson | |
| 5,766,219 A | 6/1998 | Horton | |
| 5,769,882 A | 6/1998 | Fogarty et al. | |
| 5,769,884 A | 6/1998 | Solovay | |
| 5,861,003 A | 1/1999 | Latson et al. | |
| 5,916,235 A | 6/1999 | Guglielmi | |
| 5,928,260 A | 7/1999 | Chin et al. | |
| 5,935,148 A * | 8/1999 | Villar et al. | 606/213 |
| 5,941,249 A | 8/1999 | Maynard | |
| 5,948,018 A | 9/1999 | Dereume et al. | |
| 5,951,599 A | 9/1999 | McCrory | |
| 5,976,162 A | 11/1999 | Doan et al. | |
| 6,024,754 A | 2/2000 | Engelson | |
| 6,063,104 A * | 5/2000 | Villar et al. | 606/213 |
| 6,063,111 A | 5/2000 | Hieshima et al. | |
| 6,090,063 A | 7/2000 | Makower et al. | |
| 6,096,034 A | 8/2000 | Kuiecki et al. | |
| 6,139,564 A | 10/2000 | Teoh | |
| 6,165,193 A | 12/2000 | Greene, Jr. et al. | |
| 6,165,212 A | 12/2000 | Dereume et al. | |
| 6,168,592 B1 | 1/2001 | Kupiecki et al. | |
| 6,168,622 B1 | 1/2001 | Mazzocchi | |
| 6,270,523 B1 | 8/2001 | Herweck et al. | |
| 6,299,619 B1 | 10/2001 | Greene, Jr. et al. | |
| 6,309,367 B1 | 10/2001 | Boock | |
| 6,309,413 B1 | 10/2001 | Dereume et al. | |
| 6,331,191 B1 | 12/2001 | Chobotov | |
| 6,342,068 B1 | 1/2002 | Thompson | |
| 6,344,041 B1 | 2/2002 | Kupiecki et al. | |
| 6,344,048 B1 | 2/2002 | Chin et al. | |
| 6,346,117 B1 * | 2/2002 | Greenhalgh | 606/200 |
| 6,350,270 B1 * | 2/2002 | Roue | 606/151 |
| 6,375,668 B1 | 4/2002 | Gifford et al. | |
| 6,391,037 B1 * | 5/2002 | Greenhalgh | 606/151 |
| 6,409,749 B1 | 6/2002 | Maynard | |
| 6,428,558 B1 | 8/2002 | Jones et al. | |
| 6,454,780 B1 | 9/2002 | Wallace | |
| 6,500,190 B2 | 12/2002 | Greene | |
| 6,506,204 B2 | 1/2003 | Mazzocchi | |
| 6,511,468 B1 * | 1/2003 | Cragg et al. | 604/508 |
| 6,547,804 B2 | 4/2003 | Porter et al. | |
| 6,569,190 B2 | 5/2003 | Whalen, II et al. | |
| 6,585,748 B1 * | 7/2003 | Jeffree | 606/200 |
| 6,602,261 B2 | 8/2003 | Greene, Jr. et al. | |
| 6,605,111 B2 | 8/2003 | Bose et al. | |
| 6,613,074 B1 | 9/2003 | Mitelber et al. | |
| 6,626,928 B1 | 9/2003 | Raymond | |
| 6,656,214 B1 | 12/2003 | Fogarty et al. | |
| 6,673,103 B1 | 1/2004 | Golds et al. | |
| 6,723,108 B1 | 4/2004 | Jones et al. | |
| 6,746,468 B1 | 6/2004 | Sepetka et al. | |
| 6,770,087 B2 | 8/2004 | Layne et al. | |
| 6,780,196 B2 | 8/2004 | Chin et al. | |
| 6,786,920 B2 | 9/2004 | Shannon et al. | |
| 6,790,225 B1 | 9/2004 | Shannon et al. | |
| 6,802,851 B2 | 10/2004 | Jones et al. | |
| 6,811,560 B2 | 11/2004 | Jones et al. | |
| 6,855,153 B2 | 2/2005 | Saadat | |
| 6,855,154 B2 | 2/2005 | Abdel-Gawwad | |
| 6,958,061 B2 * | 10/2005 | Truckai et al. | 606/28 |
| 6,960,217 B2 | 11/2005 | Bolduc | |
| 6,979,344 B2 | 12/2005 | Jones et al. | |
| 7,029,487 B2 | 4/2006 | Greene et al. | |
| 7,052,513 B2 | 5/2006 | Thompson | |
| 7,070,609 B2 | 7/2006 | West | |
| 7,083,632 B2 | 8/2006 | Avellanet et al. | |
| 7,083,643 B2 * | 8/2006 | Whalen et al. | 623/1.42 |
| 7,153,323 B1 * | 12/2006 | Teoh et al. | 623/1.23 |
| 7,156,871 B2 | 1/2007 | Jones et al. | |
| 7,186,263 B2 | 3/2007 | Golds et al. | |
| 7,201,762 B2 | 4/2007 | Greene, Jr. et al. | |
| 7,211,109 B2 | 5/2007 | Thompson | |
| 7,229,461 B2 | 6/2007 | Chin et al. | |
| 7,303,571 B2 | 12/2007 | Makower et al. | |
| 7,306,622 B2 | 12/2007 | Jones et al. | |
| 7,306,624 B2 | 12/2007 | Yodfat et al. | |
| 7,491,214 B2 | 2/2009 | Greene, Jr. et al. | |
| 7,520,893 B2 | 4/2009 | Rivelli, Jr. | |
| 7,569,066 B2 | 8/2009 | Gerberding et al. | |
| 7,753,931 B2 | 7/2010 | Diaz et al. | |
| 7,766,871 B2 | 8/2010 | Hirszowicz | |
| 7,803,180 B2 | 9/2010 | Burpee et al. | |
| 7,806,857 B2 | 10/2010 | Khosravi et al. | |
| 7,976,527 B2 | 7/2011 | Cragg et al. | |
| 2002/0026210 A1 * | 2/2002 | Abdel-Gawwad | 606/194 |
| 2002/0042628 A1 | 4/2002 | Chin et al. | |
| 2002/0165572 A1 * | 11/2002 | Saadat | 606/194 |
| 2002/0169473 A1 | 11/2002 | Sepetka et al. | |
| 2003/0028209 A1 * | 2/2003 | Teoh et al. | 606/191 |
| 2003/0083676 A1 | 5/2003 | Wallace | |
| 2003/0093097 A1 | 5/2003 | Avellanet et al. | |
| 2003/0135264 A1 | 7/2003 | Whalen, II et al. | |
| 2003/0181927 A1 | 9/2003 | Wallace | |
| 2003/0187473 A1 | 10/2003 | Berenstein et al. | |
| 2003/0195553 A1 | 10/2003 | Wallace et al. | |
| 2004/0010263 A1 * | 1/2004 | Boucher et al. | 606/99 |
| 2004/0098027 A1 * | 5/2004 | Teoh et al. | 606/200 |
| 2004/0158282 A1 | 8/2004 | Jondes et al. | |
| 2004/0167597 A1 | 8/2004 | Costantino et al. | |
| 2004/0181253 A1 | 9/2004 | Sepetka et al. | |
| 2005/0021077 A1 | 1/2005 | Chin et al. | |
| 2005/0033349 A1 | 2/2005 | Jones et al. | |
| 2005/0267510 A1 | 12/2005 | Razack | |
| 2006/0052816 A1 | 3/2006 | Bates et al. | |
| 2006/0058834 A1 | 3/2006 | Do et al. | |
| 2006/0079923 A1 | 4/2006 | Chhabra et al. | |
| 2006/0116709 A1 | 6/2006 | Sepetka et al. | |
| 2006/0116712 A1 | 6/2006 | Sepetka et al. | |
| 2006/0116713 A1 | 6/2006 | Sepetka et al. | |
| 2006/0149309 A1 * | 7/2006 | Paul et al. | 606/195 |
| 2006/0155323 A1 | 7/2006 | Porter et al. | |
| 2006/0206139 A1 | 9/2006 | Tekulve | |
| 2006/0235464 A1 | 10/2006 | Avellanet et al. | |
| 2006/0276831 A1 | 12/2006 | Porter | |
| 2006/0292206 A1 | 12/2006 | Kim et al. | |
| 2007/0038288 A1 | 2/2007 | Lye et al. | |
| 2007/0050008 A1 | 3/2007 | Kim et al. | |
| 2007/0055355 A1 | 3/2007 | Kim et al. | |
| 2007/0078506 A1 | 4/2007 | McCormick et al. | |
| 2007/0088387 A1 | 4/2007 | Eskridge et al. | |
| 2007/0106311 A1 | 5/2007 | Wallace et al. | |
| 2007/0150041 A1 | 6/2007 | Evans et al. | |
| 2007/0150045 A1 | 6/2007 | Ferrera | |
| 2007/0167747 A1 | 7/2007 | Borgert | |
| 2007/0168011 A1 | 7/2007 | LaDuca et al. | |
| 2007/0207186 A1 | 9/2007 | Scanlon et al. | |
| 2007/0219578 A1 | 9/2007 | Solar et al. | |
| 2007/0219610 A1 | 9/2007 | Israel | |
| 2007/0219619 A1 | 9/2007 | Dieck et al. | |
| 2007/0239261 A1 | 10/2007 | Bose et al. | |
| 2007/0276469 A1 | 11/2007 | Tenne | |
| 2007/0276470 A1 | 11/2007 | Tenne | |
| 2008/0004653 A1 | 1/2008 | Sherman et al. | |
| 2008/0033341 A1 | 2/2008 | Grad | |
| 2008/0033480 A1 | 2/2008 | Hardert et al. | |
| 2008/0039933 A1 | 2/2008 | Yodfat et al. | |
| 2008/0045996 A1 | 2/2008 | Makower et al. | |
| 2008/0114391 A1 | 5/2008 | Dieck et al. | |
| 2008/0147100 A1 | 6/2008 | Wallace et al. | |
| 2008/0221554 A1 | 9/2008 | O'Connor et al. | |
| 2008/0281350 A1 * | 11/2008 | Sepetka et al. | 606/200 |
| 2008/0319521 A1 | 12/2008 | Norris et al. | |
| 2009/0112249 A1 * | 4/2009 | Miles et al. | 606/192 |
| 2009/0192536 A1 | 7/2009 | Berez et al. | |
| 2009/0198318 A1 | 8/2009 | Berez et al. | |

(56) References Cited

U.S. PATENT DOCUMENTS

| | | |
|---|---|---|
| 2009/0287291 A1 | 11/2009 | Becking et al. |
| 2009/0287294 A1 | 11/2009 | Rosqueta et al. |
| 2009/0299326 A1 | 12/2009 | Morsi |
| 2009/0299448 A1 | 12/2009 | Timko et al. |
| 2009/0318947 A1 | 12/2009 | Garcia et al. |
| 2009/0318948 A1* | 12/2009 | Linder et al. ............... 606/191 |
| 2010/0004671 A1 | 1/2010 | Gerberding et al. |
| 2010/0004726 A1 | 1/2010 | Hancock et al. |
| 2010/0010624 A1 | 1/2010 | Berez et al. |
| 2010/0063531 A1 | 3/2010 | Rudakov et al. |
| 2010/0069948 A1 | 3/2010 | Veznedaroglu |
| 2010/0094335 A1 | 4/2010 | Gerberding et al. |
| 2010/0106240 A1 | 4/2010 | Duggal et al. |
| 2010/0131002 A1 | 5/2010 | Connor et al. |
| 2010/0152828 A1 | 6/2010 | Pakbaz et al. |
| 2010/0262124 A1 | 10/2010 | Hirszowicz et al. |
| 2010/0274276 A1 | 10/2010 | Chow et al. |
| 2010/0274346 A1 | 10/2010 | Chouinard |
| 2010/0280590 A1 | 11/2010 | Sun et al. |
| 2011/0166588 A1 | 7/2011 | Connor et al. |
| 2012/0004682 A1 | 1/2012 | Connor |

FOREIGN PATENT DOCUMENTS

| | | |
|---|---|---|
| JP | 2000-512515 A | 9/2000 |
| JP | 2003-70795 A | 3/2003 |
| JP | 2003-508107 A | 3/2003 |
| JP | 2003-508107 A | 3/2003 |
| JP | 2004-520881 A | 7/2004 |
| JP | 2004-520881 A | 7/2004 |
| WO | WO-9618343 A1 | 6/1996 |
| WO | WO-97/19643 A2 | 6/1997 |
| WO | WO-00/72781 A2 | 12/2000 |
| WO | WO-01/15608 A1 | 3/2001 |
| WO | WO-02/051320 A2 | 7/2002 |
| WO | WO-2006084077 A1 | 8/2006 |
| WO | WO-2009/134337 A1 | 11/2009 |
| WO | WO-2009134337 A1 | 11/2009 |

OTHER PUBLICATIONS

"International Application Serial No. PCT/US2009/02537, Written Opinion mailed Jun. 17, 2009".

"European Application Serial No. 09739140.3, Office Action mailed Dec. 9, 2010", 2 pgs.

"International Application Serial No. PCT/US2009/02537, International Preliminary Report on Patentability dated Jan. 13, 2011", 4 pgs.

"Japanese Application Serial No. 2011-507419, Office Action mailed May 29, 2012", (w/ English Translation), 4 pgs.

"Chinese Application Serial No. 200980123478.0, Office Action mailed Jul. 17, 2012", (w/ English Translation), 15 pgs.

"Japanese Application Serial No. 2011-507419, Office Action mailed Sep. 18, 2012", (w/ English Translation), 5 pgs.

"Japanese Application Serial No. 2011-507419, Response filed Aug. 23, 2012 to Office Action mailed May 29, 2012", (w/ English Translation of Claims), 13 pgs.

* cited by examiner

ANEURYSM OCCLUSION DEVICE

CLAIM OF PRIORITY

This application is a U.S. National Stage Filing under 35 U.S.C. 371 and claims the benefit of priority under 35 U.S.C. §120 to International Patent Application Serial No. PCT/US2009/002537, filed Apr. 24, 2009, and published on Nov. 5, 2009 as WO 2009/134337, which is incorporated by reference herein in its entirety, and through which priority is also claimed to:

(1) Robert A. Connor's U.S. Provisional Patent Application Ser. No. 61/126,047, entitled FLOW OF SOFT MEMBERS INTO A NET TO EMBOLIZE AN ANEURYSM, which received a filing date of May 1, 2008, and which is incorporated by reference herein in its entirety; and (2) Robert A. Connor's U.S. Provisional Patent Application Ser. No. 61/126,027, entitled NET FILLED WITH SOFT MEMBERS TO EMBOLIZE AN ANEURYSM, which received a filing date of May 1, 200, and which is incorporated by reference herein in its entirety.

BACKGROUND

An aneurysm is an abnormal bulging or ballooning of a blood vessel. Rupture of brain aneurysms can cause stroke, death, or disability. Around at least one-third of people who have a brain aneurysm that ruptures will die within 30 days of the rupture. Of the survivors, around half of the survivors suffer some permanent loss of brain function. Many aneurysms are not identified until they rupture. However, identification of intact aneurysms is increasing due to increased outpatient imaging. Ruptured aneurysms must be treated to stop the bleeding or to prevent re-bleeding. Intact aneurysms may or may not be treated to prevent rupture, depending on their characteristics. Wide neck aneurysms are less prone to rupture, but harder to treat. In the U.S., it has been estimated that over 10 million people have brain aneurysms and 30,000 people each year have a brain aneurysm that ruptures.

Several approaches can be used to treat brain aneurysms. These different approaches can be divided into three categories: (1) approaches involving treatment outside the vessel; (2) approaches involving treatment inside the aneurysm; and (3) approaches involving treatment in the parent vessel. Some of these approaches can be used together. Each of these approaches has some disadvantages, as discussed below.

1. Treatment Outside the Vessel

Clipping: Clipping is the application of a small clip to the aneurysm neck from outside the vessel to seal off the aneurysm. For most brain aneurysms, this involves invasive surgery including removing a section of the skull. Clipping began in the 1930's and is well-established. Clipping is more common in the U.S. than in Europe. Around half of all aneurysms are treated by clipping. However, clipping is decreasing. There are many aneurysm clips. Potential disadvantages of clipping can include: significant health risks associated with major surgery of this type; and long recovery times, even when the surgery itself goes well.

2. Treatment Inside the Aneurysm:

Metal Coils: Metal coiling is the endovascular insertion of metal coils into the aneurysm to reduce blood flow and promote embolization in the aneurysm. Historically, metal coils have been platinum. Coils are more common in Europe than in the U.S. There are many examples of metal coils. Potential disadvantages of metal coils can include: low percentage of aneurysm volume filled—and low occlusion is associated with a higher risk of rupture; compaction of coils over time; risk of recanalization; potential prolapse of coils into the parent vessel; difficulty later clipping aneurysms filled with metal coils, if needed; pressure from the coils on surrounding brain tissue; inability of coils to treat all aneurysms; and expense of metal coils (especially platinum coils).

Combination Metal/Textile/Foam/Gel Coils: Coils with a combination of metal and other materials can be used to try to achieve greater occlusion volume than metal coils alone. These other materials include textile, foam, and gel elements. Textile strands can be woven into the coils to add bulk. Coils can be covered with soft foam. Gel elements can be strung together into elongated structures. Examples of such approaches for embolizing aneurysms include: U.S. Pat. No. 5,382,259 (Phelps et al.), U.S. Pat. No. 5,522,822 (Phelps et al.), U.S. Pat. No. 5,690,666 (Berenstein et al.), U.S. Pat. No. 5,718,711 (Berenstein et al.), U.S. Pat. No. 5,749,894 (Engelson), U.S. Pat. No. 5,976,162 (Doan et al.), U.S. Pat. No. 6,024,754 (Engelson), U.S. Pat. No. 6,299,619 (Greene, Jr. et al.), U.S. Pat. No. 6,602,261 (Greene, Jr. et al.), U.S. Pat. No. 6,723,108 (Jones et al.), U.S. Pat. No. 6,979,344 (Jones et al.), U.S. Pat. No. 7,070,609 (West), and U.S. Pat. No. 7,491,214 (Greene, Jr. et al.), and U.S. Patent Applications 20040158282 (Jones, Donald et al.), 20050267510 (Razack, Nasser), and 20060058834 (Do, Hiep et al.). Potential disadvantages of combination coils can include: remaining gaps between loops; compaction of coils over time; risk of recanalization; potential prolapse of coils into the parent vessel; difficulty clipping aneurysms filled with coils with metal components later if needed; pressure from the coils on surrounding brain tissue; inability of coils to treat all aneurysms; and expense of metal coils.

Inflatable Balloons: Approximately two decades ago, there were numerous efforts to treat aneurysms by permanently filling them with inflatable balloons. These efforts were largely abandoned due to the risks of balloon deflation, prolapse into the parent vessel, aneurysm rupture, and recanalization. There are, however, examples of relatively recent art using inflatable balloons to treat aneurysms: U.S. Pat. No. 6,569,190 (Whalen et al.) and U.S. Pat. No. 7,083,643 (Whalen et al.), and U.S. Patent Applications 20030135264 (Whalen et al.), 20030187473 (Berenstein, Alejandro et al.), 20060292206 (Kim, Steven et al.), 20070050008 (Kim, Steven et al.), and 20070055355 (Kim, Steven et al.). Potential disadvantages of using inflatable balloons to permanently fill aneurysms can include: balloon deflation; prolapse of the balloon into the parent vessel; aneurysm rupture due to balloon pressure; and recanalization.

Manually-Activated Mesh Occluders: Another approach to treating aneurysms involves inserting into the aneurysm a mesh structure, generally metal, that can be expanded or contracted by human-controlled mechanical motion so as to block the aneurysm neck and/or to fill the main volume of the aneurysm. For example, a wire structure can be inserted through the aneurysm neck in a narrow configuration and then transformed into an "hour-glass" shape that collapses to block the aneurysm neck when activated by a human controller. Examples of metal structures that occlude the aneurysm by manually-activated expansion or contraction include: U.S. Pat. No. 5,928,260 (Chin et al.), U.S. Pat. No. 6,344,048 (Chin et al.), U.S. Pat. No. 6,375,668 (Gifford et al.), U.S. Pat. No. 6,454,780 (Wallace), U.S. Pat. No. 6,746,468 (Sepetka et al.), U.S. Pat. No. 6,780,196 (Chin et al.), and U.S. Pat. No. 7,229,461 (Chin et al.), and U.S. Patent Applications 20020042628 (Chin, Yem et al.), 20020169473 (Sepetka, Ivan et al.), 20030083676 (Wallace, Michael), 20030181927 (Wallace, Michael), 20040181253 (Sepetka, Ivan et al.), 20050021077 (Chin, Yem et al.), 20060155323 (Porter, Stephen et al.), 20070088387 (Eskridge, Joseph et al.), 20070106311 (Wallace, Michael et al.), and 20080147100 (Wallace, Michael). Potential disadvantages of such manually-activated metal occluders include: difficulty engaging the necks of wide-neck aneurysms; difficulty filling irregularly-shaped aneurysms with standard-shaped mesh structures; risk of rupture when pinching the aneurysm neck or pushing on the aneurysm walls; and protrusion of the proximal portion of "hour-glass" designs into the parent vessel.

Self-Expanding Standard-Shape Occluders: Another approach to treat aneurysms uses standard-shaped structures that self-expand when released into the aneurysm. For example, the structure may be a mesh of "shape memory" metal that automatically expands to a standard shape when released from the confines of the catheter walls. As another example, the structure may be a gel that expands to a standard shape when exposed to moisture. Examples of such self-expanding structures include: U.S. Pat. No. 5,766,219 (Horton), U.S. Pat. No. 5,916,235 (Guglielmi), U.S. Pat. No. 5,941,249 (Maynard), U.S. Pat. No. 6,409,749 (Maynard), U.S. Pat. No. 6,506,204 (Mazzocchi), U.S. Pat. No. 6,605,111 (Bose et al.), U.S. Pat. No. 6,613,074 (Mitelberg et al.), U.S. Pat. No. 6,802,851 (Jones et al.), U.S. Pat. No. 6,811,560 (Jones et al.), U.S. Pat. No. 6,855,153 (Saadat), U.S. Pat. No. 7,083,632 (Avellanet et al.), U.S. Pat. No. 7,306,622 (Jones et al.), and U.S. Pat. No. 7,491,214 (Greene, Jr. et al.), and U.S. Patent Applications 20030093097 (Avellanet, Ernesto et al.), 20030195553 (Wallace, Michael et al.), 20050033349 (Jones, Donald et al.), 20060052816 (Bates, Brian et al.), and 20060235464 (Avellanet, Ernesto et al.) and WIPO Patents WO/2006/084077 (Porter, Stephen et al.) and WO/1996/018343 (McGurk et. al.). Potential disadvantages of such self-expanding standard-shape structures can include: risk of prolapse into the parent vessel, especially for wide-neck aneurysms; difficulty occluding irregularly-shaped aneurysms with standard shape structures and associated risk of recanalization; and difficulty generating the proper amount of force (not too much or too little) when engaging the aneurysm walls with a standard-shaped self-expanding structure.

Self-Expanding Custom-Modeled Occluders: A variation on self-expanding standard-shape occluders (discussed above) are self-expanding occluders that are custom modeled before insertion so as to fit the shape of a particular aneurysm. As an example sequence—the aneurysm can be imaged, the image is used to custom model the occluding structure, the occluding structure is compressed into a catheter, the occluding structure is inserted into the aneurysm, and the occluding structure then self-expands to fill the aneurysm. The occluding structure may be made from a gel that expands upon contact with moisture. Examples in the related art involving self-expanding custom-modeled occluding structures include: U.S. Pat. No. 5,766,219 (Horton), U.S. Pat. No. 6,165,193 (Greene, Jr. et al.), U.S. Pat. No. 6,500,190 (Greene, Jr. et al.), U.S. Pat. No. 7,029,487 (Greene, Jr. et al.), and U.S. Pat. No. 7,201,762 (Greene, Jr. et al.), and U.S. Patent Application 20060276831 (Porter, Stephen et al.). Potential disadvantages of self-expanding custom-modeled occluders can include: the complexity and expense of imaging and modeling irregularly-shaped aneurysms; difficulty compressing larger-size structures into a catheter; difficulty inserting the occluding structure in precisely the correct position; and difficulty getting a gelatinous surface to anchor solidly to aneurysm walls.

Congealing Liquid or Gel: Another approach to treating aneurysms involves filling the aneurysm with a liquid or gel that congeals rapidly. Examples of this approach include the following: U.S. Pat. No. 6,569,190 (Whalen et al.), U.S. Pat. No. 6,626,928 (Raymond et al.), U.S. Pat. No. 6,958,061 (Truckai et al.), and U.S. Pat. No. 7,083,643 (Whalen et al.), and U.S. Patent Application 20030135264 (Whalen et al.). Potential disadvantages of a congealing liquid or gel can include: leakage of the congealing substance into the parent vessel, potentially causing a stroke; difficulty filling the entire aneurysm if the substance begins to congeal before the aneurysm is full; and seepage of toxic substances into the blood stream.

Biological or Pharmaceutical Agents: Biological and/or pharmaceutical agents can enhance the performance of a variety of mechanical treatment methods for aneurysms. For example, they can speed up the natural embolization process to occlude the aneurysm. Some examples of using biological and/or pharmaceutical agents to treat aneurysms include: U.S. Patent Applications 20060206139 (Tekulve, Kurt J.), 20070168011 (LaDuca, Robert et al.), and 20080033341 (Grad, Ygael). Currently, biological and/or pharmaceutical approaches are not sufficient as stand alone treatment approaches for many cases. Accordingly, they share most of the potential disadvantages of the baseline approach to which the biological or pharmaceutical agents are added.

Embolic-Emitting Expanding Members: Another approach involves an expanding member within the aneurysm that emits embolic elements into the aneurysm. Examples of such expanding members include bags, meshes, and nets. Examples of embolic elements include coils and congealing liquids. This can be viewed as another way to block the aneurysm neck while delivering embolics into the volume of the aneurysm. For example, the distal portion of an expanding bag may leak embolic elements into the aneurysm, but the proximal portion of the expanding member does not leak embolics into the parent vessel. Examples of this approach include: U.S. Pat. No. 6,547,804 (Porter et al.) and U.S. Patent Applications 20040098027 (Teoh, Clifford et al.), 20060079923 (Chhabra, Manik et al.), and 20080033480 (Hardert, Michael). Potential disadvantages are as follows. Since the expanding member "leaks," it may have insufficient expansion force to adequately anchor against the aneurysm walls or to seal off the aneurysm neck. As a result of poor anchoring, the bag may prolapse into the parent vessel. Also, as a result of poor sealing of the aneurysm neck, embolics may leak into the parent vessel.

Shape Memory Structures inside Expanding Members: A variation on the shape memory approach above involves the addition of an expanding member around the shape memory structure. Examples of this approach include: U.S. Pat. No. 5,861,003 (Latson et al.), U.S. Pat. No. 6,346,117 (Greenhalgh), U.S. Pat. No. 6,350,270 (Roue), U.S. Pat. No. 6,391,037 (Greenhalgh), and U.S. Pat. No. 6,855,153 (Saadat). The potential disadvantages of this approach are similar to those for uncovered shape memory occluders: risk of prolapse into the parent vessel, especially for wide-neck aneurysms; difficulty occluding irregularly-shaped aneurysms with standard shape structures and associated risk of recanalization; and difficulty generating the proper amount of force (not too much or too little) when engaging the aneurysm walls with a standard-shaped self-expanding structure.

Accumulating Coils inside Expanding Members: A variation on the standard coiling approach above involves the addition of an expanding member around the accumulating coils. Examples of this approach include: U.S. Pat. No. 5,334,210 (Gianturco), U.S. Pat. No. 6,585,748 (Jeffree), and U.S. Pat. No. 7,153,323 (Teoh et al.), and U.S. Patent Applications 20060116709 (Sepetka, Ivan et al.), 20060116712 (Sepetka, Ivan et al.), and 20060116713 (Sepetka, Ivan et al.). Potential disadvantages of this approach are similar to those for coils alone, including: compaction of coils over time; risk of recanalization due to "bumpy" coil-filled expanding member; difficulty clipping aneurysms filled with metal coils later if needed; pressure from the coils on surrounding brain tissue; inability to treat all aneurysms; and expense of metal coils (especially platinum coils).

3. Treatment in the Parent Vessel:

Standard (High-Porosity) Stent: A stent is a structure that is inserted into a vessel in a collapsed form and then expanded into contact with the vessel walls. Standard stents are generally highly porous, metal, and cylindrical. A high-porosity stent allows blood to flow through the stent walls if there are any branching vessels or other openings in the vessel walls. Blood flow through a stent wall into a branching vessel is desirable; blood flow through a stent wall into an aneurysm is not. Accordingly, a high-porosity stent in the parent vessel is not a good stand-alone aneurysm treatment. A high-porosity in the parent vessel can, however, help to keep coils or other embolic members from escaping out of the aneurysm into the parent vessel. Examples of this approach include: U.S. Pat. No. 6,096,034 (Kupiecki et al.), U.S. Pat. No. 6,168,592 (Kupiecki et al.), U.S. Pat. No. 6,344,041 (Kupiecki et al.), U.S. Pat. No. 7,211,109 (Thompson), and U.S. Pat. No. 7,303,571 (Makower et al.), and U.S. Patent Application 20080045996 (Makower, Joshua et al.). Potential disadvantages of this approach can include many of the problems associated with use of the embolic members alone. For example, using a high-porosity stent in the parent vessel in combination with coils in the aneurysm still leaves the following disadvantages of using coils alone: low percentage of aneurysm volume filled (and low occlusion is associated with a higher risk of rupture); compaction of coils over time; significant risk of recanalization; difficulty clipping aneurysms filled with metal coils later if needed; pressure from the coils on surrounding brain tissue; inability of coils to treat all aneurysms; and expense of metal coils (especially platinum coils).

Uniformly Low-Porosity Stent: Another approach involves inserting a uniformly low-porosity stent into the parent vessel. The low-porosity stent blocks the flow of blood through the stent walls into the aneurysm, causing beneficial embolization of the aneurysm. For example, the stent may have one or more layers that are impermeable to the flow of liquid. Unlike a standard (high-porosity) stent, this approach can be used as a stand-alone aneurysm treatment. Examples of this approach include: U.S. Pat. No. 5,645,559 (Hachtman et al.), U.S. Pat. No. 6,270,523 (Herweck et al.), U.S. Pat. No. 6,331,191 (Chobotov), U.S. Pat. No. 6,342,068 (Thompson), U.S. Pat. No. 6,428,558 (Jones et al.), U.S. Pat. No. 6,656,214 (Fogarty et al.), U.S. Pat. No. 6,673,103 (Golds et al.), U.S. Pat. No. 6,786,920 (Shannon et al.), and U.S. Pat. No. 6,790,225 (Shannon et al.), and U.S. Patent Application 20080319521 (Norris, Stephanie et al.). Potential disadvantages of this approach can include: undesirably blocking blood flow to branching vessels that are close to the aneurysm and are covered by the stent wall; and difficulty achieving a snug fit across the neck of the aneurysm if the parent vessel is curved, twisted, or forked.

Uniformly Intermediate-Porosity Metal Stent: This approach pursues creation of a stent with a uniform intermediate porosity that provides a compromise between the benefits of a high-porosity stent in the parent vessel (good blood flow to nearby branching vessels) and the benefits of a low-porosity stents in the parent vessel (blocking blood flow to the aneurysm). Examples of this approach include: U.S. Pat. No. 5,769,884 (Solovay) and U.S. Pat. No. 7,306,624 (Yodfat et al.) and U.S. Patent Applications 20070219619 (Dieck, Martin et al.), 20070239261 (Bose, Arani et al.), and 20080039933 (Yodfat, Ofer et al.). The main potential disadvantage of this approach is that it may do neither function well. It may unreasonably block flow to a branching vessel (causing a stroke) and inadequately block blood flow to the aneurysm (leaving it vulnerable to rupture).

Pre-Formed Differential Porosity Stent: This approach involves creates a stent with different levels of porosity for different wall areas, before the stent is inserted into the parent vessel. The goal is to place wall areas with high porosity over openings to branching vessels and to place wall areas with low porosity over the neck of the aneurysm. Examples of this approach include: U.S. Pat. No. 5,723,004 (Dereume et al.), U.S. Pat. No. 5,948,018 (Dereume et al.), U.S. Pat. No. 5,951,599 (McCrory), U.S. Pat. No. 6,063,111 (Hieshima et al.), U.S. Pat. No. 6,165,212 (Dereume et al.), U.S. Pat. No. 6,309,367 (Boock), U.S. Pat. No. 6,309,413 (Dereume et al.), U.S. Pat. No. 6,770,087 (Layne et al.), U.S. Pat. No. 7,052,513 (Thompson), and U.S. Pat. No. 7,186,263 (Golds et al.), and U.S. Patent Applications 20070207186 (Scanlon, John et al.), 20070219610 (Israel, Henry M.), 20070239261 (Bose, Arani et al.), 20070276469 (Tenne, Dirk), 20070276470 (Tenne, Dirk), and 20080004653 (Sherman, Darren et al.). Potential disadvantages of this approach can include: difficultly and expense involved in matching a specific anatomic configuration (curvature, branching, neck size, etc) with a set of pre-formed stents; and difficulty of precise placement of the stent to properly align the porous and non-porous areas with branching vessels and the aneurysm, respectively.

Post-Implantation Filling Between Stent Wall and Vessel Wall: Unlike the previous approach involving a stent with differential porosity across different wall areas before implantation, this approach creates differential porosity across different wall areas after the stent is implanted. In particular, this approach involves filling the gap between the stent wall and the vessel wall with an embolizing substance such as a congealing liquid or gel. Examples of this approach include: U.S. Pat. No. 5,769,882 (Fogarty et al.), U.S. Pat. No. 5,951,599 (McCrory), and U.S. Pat. No. 6,096,034 (Kupiecki et al.), and U.S. Patent Application 20070150041 (Evans, Michael et al.). Potential disadvantages of this approach can include: difficulty injecting the embolizing substance through the stent wall without having it leak back into the parent vessel; potential leakage of embolizing substance into branching vessels; challenges containing the embolic material within curving vessels or vessels with irregular walls; and difficulty of use to fill narrow-neck aneurysms.

Post-Implantation Surface Modification: This approach creates differential porosity across different wall areas after stent implantation by targeted surface modification using chemicals or targeted energy. For example, exposure of the portion of the stent wall covering the aneurysm neck to certain chemicals or energy may cause that porosity of the wall to decrease. An example of this approach is U.S. Pat. No. 7,156,871 (Jones et al.). Potential disadvantages of this approach can include: difficulty getting a good seal between the stent wall and aneurysm neck in curved, twisted, or branching vessels; and negative effects of chemicals or targeted energy on surrounding vessel or brain tissue.

In sum, although there has been significant progress in developing options for treating brain aneurysms, there are still high rates of death and disability and still disadvantages to the treatment options available.

OVERVIEW

This document describes aneurysm treatment devices and methods that can provide advantages over current treatment options. In an example, a flexible net or flexible mesh can be inserted into the aneurysm and then filled. Such filling can include using a liquid flow carrying soft compressible fill members (such as micro-sponges) that do not pass through the net. The net can be configured such that the openings in the net are too small to allow such passage, but are large enough to allow enough liquid flow to load the net with the fill members.

As the flexible net is filled with these soft compressible fill members, the net can expand into gentle but engaging contact with the aneurysm walls. Unlike coils and most other approaches, the filled expanded flexible net can occlude virtually the entire volume of the aneurysm—even for irregularly shaped aneurysms. Unlike expanding balloons or bags that have smooth surfaces, the porous surface of the net or mesh enclosure, with the soft fill members carried inside, can frictionally engage the interior aneurysm walls, thereby holding the net in place within the aneurysm.

This approach can overcome many potential disadvantages of other approaches, as discussed below (without limiting the scope of the present approach to require any particular one or all of the advantages discussed herein). Unlike clipping, it is a less-invasive endovascular treatment. Unlike coils, the present approach can be used to fill a high percentage of aneurysm volume, such as for promoting rapid embolization and less recanalization. It can also preserve the option of subsequent clipping, if needed later. It does not deflate or compress over time. The porous surface of the net or mesh enclosure, filled with soft compressible fill members, can engage the walls of the aneurysm to hold the filled structure in place and to inhibit or prevent it from prolapsing into the parent vessel. In the present approach, there are no metal components poking or pinching the aneurysm walls, which could potentially lead to rupture. The present device can conform to the walls of irregularly-shaped aneurysms. It does not require complex pre-insertion imaging and modeling. In the present approach, there are no unhealthy chemicals to potentially seep into the bloodstream. Blood flow to branching vessels is not blocked.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5, FIG. 6, FIG. 7, and FIG. 8 correspond to an example of the four stages of device implementation for which the distal end of the device (inside the body) is shown in FIGS. 1-4.

DETAILED DESCRIPTION

Figure 1:
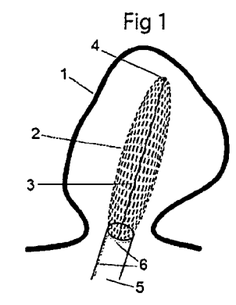
FIG. 1 shows an example of portions of an aneurysm occlusion device before the flow of soft fill members has started.

FIG. 1 shows an example of portions of an aneurysm occlusion device before the flow of soft fill members has started. In this example, an elongated flexible intravascular guide member, such as a catheter 5, can be percutaneously introduced into a blood vessel, and intravascularly guided toward an aneurysm 1, such as by using fluoroscopic or other imaging guidance. The catheter 5 can include a lumen, such as extending between its proximal and distal ends. The catheter 5 can also include a net or mesh enclosure 2. In various illustrative examples, the net or mesh enclosure 2 can include at least one of a nylon material, a polypropylene material, a polyester material, a polytetrafluorethylene material, or a polytetrafluoroethene material. The net or mesh enclosure 2 can be located at a distal end of the catheter 5. For example, the net or mesh enclosure 2 can protrude from the distal end of the catheter 5, outside of the lumen, during introduction of the catheter 5 into the blood vessel. The net or mesh enclosure 2 can also be located within the distal end of the catheter 5 during introduction of the catheter 5 into the blood vessel, with the net or mesh enclosure 2 later being pushed out of the lumen of the catheter 5 and into the aneurysm 1, such as by a guidewire or other elongated member 3, which can extend through the lumen of the catheter 5, such as from the proximal end of the catheter 5 to the distal end of the catheter 5. The net or mesh enclosure 2 can also be introduced into and through the lumen of the catheter 5 after the catheter 5 has been introduced into the blood vessel, such as by using the guidewire or other elongated member 3 to push the net or mesh enclosure 2 through the lumen of the catheter 5 from its proximal end to and out of its distal end. The guidewire or other member elongated member 3 can include a relatively blunt tip, such as to push the net or mesh enclosure 2. The guidewire or other member elongated member 3 can include a shape memory or other curvature, such as to push the net or mesh enclosure 2 longitudinally out of a lumen of the catheter 5, then turning at least somewhat perpendicularly thereto to push the net or mesh enclosure 2 out into the aneurysm 1, such as in a situation where the aneurysm 1 extends in an at least somewhat perpendicular direction from the blood vessel.

In the example of FIG. 1, the net or mesh enclosure 2 is shown in an example of its initially folded or compressed form. It can take this relatively collapsed form while it is being intravascularly guided through the body or while it is being inserted into the aneurysm 1. In the example of FIG. 1, a distal location 4 on the net or mesh enclosure 2 can be configured to receive or to be attached to a distal end of the guidewire or other member 3, which extends out of the lumen of the catheter 5. In an example, such attachment can be accomplished using a threadable engagement. For example, threads on the distal end of the guidewire or other member 3 can be screwed in (e.g., using a clockwise rotation) into a corresponding threaded receptacle that can be included in or affixed to the distal portion of the net or mesh enclosure 2, such as at the location 4. Later, the wire or other member 3 can be rotated in the other direction (e.g., using a counter-clockwise rotation), such as at its proximal end at a remote location outside the body. This can detach the wire or other member 3 from the net or mesh enclosure 2, which can allow the wire or other member 3 to be withdrawn through the lumen of the catheter, either by itself, or by together with the catheter 5.

In the example of FIG. 1, a proximal portion of the net or mesh enclosure 2 can be attached to the distal end of the catheter 5. The net or mesh enclosure 2 can include a proximal opening, such that the net or mesh enclosure 2 can be in open communication with the lumen of the catheter at the distal end of the catheter 5. Such attachment be accomplished using a closure 6. In an example, the closure 6 can include a cord that can weave through an elastic circular pathway that can be provided around the proximal opening of the net or mesh enclosure 2. The cord can also weave through a ring of perforations or other holes in the wall of the distal end of the catheter 5. The cord can extend through the lumen of the catheter 5. The cord can later be pulled from its proximal end at a remote location outside the body. This can detach the net or mesh enclosure 2 from the catheter 5, with the opening of the net or mesh enclosure 2 closed.

Figure 2:
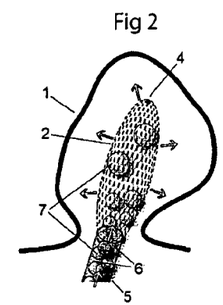
FIG. 2 shows an example of the net or mesh enclosure after being introduced into an aneurysm, after a guidewire or other member has been detached and extracted from the lumen of the catheter, and after the flow of soft fill members has started.

FIG. 2 shows an example of the net or mesh enclosure 2 after the net or mesh enclosure 2 has been introduced into the aneurysm 1, and the guidewire or other member 3 has been detached and extracted from the lumen of the catheter 5. In this example, the net or mesh enclosure 2 can be expanded with a liquid flow including multiple soft and compressible fill members 7. In various illustrative examples, the fill members 7 can include or consist essentially of non-inflammatory, implantably non-biodegradable, and anti-bacterial or anti-microbial material. In various illustrative examples, the fill members 7 can include or consist essentially of at least one of a sponge material, a foam material, or a gel material.

In various illustrative examples, the fill members 7 can include or consist essentially of one or more of the following, in isolation or in one or more polymers—cellulose, collagen, acetate, alginic acid, carboxy methyl cellulose, chitin, collagen glycosaminoglycan, divinylbenzene, ethylene glycol, ethylene glycol dimethylmathacrylate, ethylene vinyl acetate, hyaluronic acid, hydrocarbon polymer, hydroxyethylmethacrylate, methlymethacrylate, polyacrylic acid, polyamides, polyesters, polyolefins, polysaccharides, polyurethane, polyvinyl alcohol, silicone, urethane, and vinyl stearate. In various illustrative examples, the fill members can include or be impregnated with a thrombogenic agent. In various illustrative examples, at least one or all of the fill members can be configured to be shaped as at least one of a ball or sphere, an ovoid, an ellipsoid, or a polyhedron. In an example, the fill members 7 can include a Shore OO value, indicative of softness or hardness, within a range of about 5 to about 50. This can provide appropriate compressibility to fill the net or mesh enclosure 2 to push gently outward against the aneurysm walls. In an example, the fill members 7 can include a diameter or like size that is within a range of about 50 micrometers to about 2000 micrometers. In an example, the various fill members 7 can also be of substantially uniform size.

In an example, the fill members 7 can be introduced into the net or mesh enclosure 2 through the lumen in the catheter 5 and the proximal opening in the net or mesh enclosure 2. The lumen in the catheter 5 can be used to provide a liquid flow conduit. A continuous flow of liquid through the lumen in the catheter 5 can be used to carry the fill members 7 through the proximal opening of the net or mesh enclosure 2 and into the net or mesh enclosure 2 that is located in the aneurysm. Examples of the liquid can include sterile saline or plasma. The openings in the net or mesh enclosure 2 are big enough to pass enough liquid flow through such openings to carry enough of the fill members 7 through the proximal opening of the net or mesh enclosure 2 and into the net or mesh enclosure 2 to fill the net or mesh enclosure 2 with the fill members 7. This permits the net or mesh enclosure 2 to be expanded by the fill members 7 such that it substantially fills and occludes the aneurysm 1. In an example, the net or mesh enclosure 2 can include openings in the net or mesh enclosure that allow portions of at least some of the fill members to partially protrude out from the net or mesh enclosure—this can assist in conformal gripping of the interior aneurysm wall, however, it is not required.

In an example, this flow can be controlled from a remote location outside the body. As the liquid flow carrying the fill members 7 enters the interior of the net or mesh enclosure 2, the liquid passes out of the net or mesh enclosure 2, such that the soft and compressible fill members 7 can be trapped within the net or mesh enclosure 2. The accumulating soft and compressible fill members 7 within the net or mesh enclosure 2 can gently expand the net or mesh enclosure 2, such as into contour-conforming contact with the aneurysm wall of the interior of the aneurysm 1. Due to the multiplicity of the soft and compressible fill members 7, their softness, and the flexibility of the material of the net or mesh enclosure 2, the expanding net or mesh enclosure 2 can conform to the specific contours of the aneurysm wall, such as in a manner that can be difficult to achieve with metal meshes or with balloons or bags.

Figure 3:
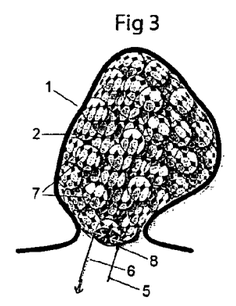
FIG. 3 shows an example of a net or mesh enclosure having been filled with multiple soft fill members, and having filled the aneurysm, and in which a proximal opening of the net or mesh enclosure is being closed-off.

FIG. 3 shows an example of the net or mesh enclosure 2 having been filled with multiple soft fill members 7, and having filled the aneurysm 1. In this example, the proximal opening 8 in the net or mesh enclosure 2 is shown closing using the closure 6. The closure 6 can be associated with the proximal opening 8, and the closure 6 can be configured to be actuated to reduce a size of the proximal opening 8 after the net or mesh enclosure has been expanded by filling it with the fill members 7. In an example, such remote actuation can include retracting a cord that can be used as the closure 6 to close the proximal opening 8 in the net or mesh enclosure 2. In an example, such a cord closure 6 can be pulled through the lumen of the catheter 5, such as from a proximal end of the cord closure 6 that is at remote location outside the body. Pulling on a proximal end of the cord closure 6 can also detach a portion of the cord closure 6 that can remain with the net or mesh enclosure 2 to hold its proximal opening 8 closed. This can be accomplished by providing a tie-off as the left-behind portion of the closure 6. The tie-off can include a ratcheting or other one-way engagement feature. A more proximal portion of the closure 6 can include a pre-weakened portion that can serves as a separation location, at which the left-behind portion of the closure 6 can detach from the cord when a proximal end of the cord is pulled from outside of the body and the proximal opening 8 has been drawn shut. In various other examples, the closure 6 can include one or more of a wire, a tie-off, a threaded member, a shape-memory material, a clasp, an adhesive, or a fusion.

The remote actuation of the closure 6 can also detach the net or mesh enclosure 2 from the distal end of catheter 5. This can close off an elastic circular proximal opening 8 in proximal portion of the net or mesh enclosure 2, such as described above, through which the liquid flow had carried multiple soft fill members 7, which had previously flowed out from the lumen of the catheter 5, through the proximal opening 8, and into the net or mesh enclosure 2. Closing off the proximal opening 8 in the net or mesh enclosure 2 can permanently trap the multiple soft fill members 7 inside of the net or mesh enclosure 2, such that the net or mesh enclosure 2 can be in contour-conforming contact with the interior walls of aneurysm 1. Such filling of the aneurysm 1 promotes blood clotting in the interstices between the fill members 7 and the openings of the net or mesh enclosure 2. This effectively occludes the aneurysm, thereby inhibiting its rupture.

Figure 4:
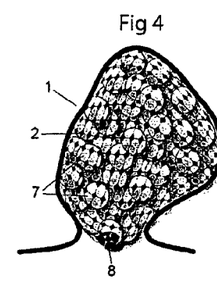
FIG. 4 shows an example in which the net or mesh enclosure has completely filled the aneurysm, the proximal opening has been substantially closed, and in which the catheter has been removed from the blood vessel and the body.

FIG. 4 shows an example in which the net or mesh enclosure 2 has completely filled the aneurysm 1, and in which the catheter 5 has been removed from the blood vessel and the body. This leaves the net or mesh enclosure 2 fully expanded into contour-conforming contact with the interior walls of aneurysm 1. The gentle, frictional, and contour-conforming contact between the walls of the aneurysm and the fibers or other elements of the net or mesh enclosure 2 helps to keep the filled net or mesh enclosure 2 securely lodged within the aneurysm 1. The presence of the filled net or mesh enclosure 2 within the aneurysm 1 can result in a substantially immediate reduction in blood flow through the aneurysm 1. This should promote embolization. Such embolization, in turn, can help attach the net or mesh enclosure 2 to the interior walls of the aneurysm 1 in an even more secure manner.

FIGS. 5-8 show an example of how the proximal end (outside the body) of a catheter can be configured and manipulated in correspondence with the distal end (within the body) configurations such as shown in the examples of FIGS. 1-4.

Figure 5:
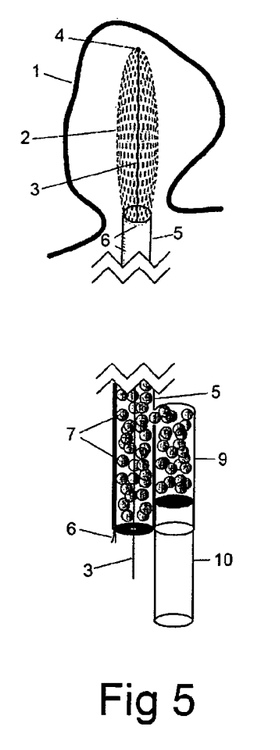
FIG. 5, FIG. 6, FIG. 7, and FIG. 8 show an example of how a proximal end of a catheter (outside the body) can be configured to be successively manipulated by the user.

FIG. 5 shows an example of the configuration of a proximal end of a catheter, corresponding to the configuration of the distal end shown in FIG. 1. In FIG. 5, the distal end (within the body) is shown at the top of FIG. 5, the proximal end (outside the body) is shown at the bottom of FIG. 5, and the zig-zag lines indicate that FIG. 5 does not show the full length of the catheter between these ends.

In the example of FIG. 5, the elongated member 3, the catheter 5, and a cord or cord-like closure 6 (that appear at or near the distal portion at the top of FIG. 5) can continue (e.g., through the intermediate portion of the catheter 5 that is not shown in FIG. 5) to the proximal end shown at the bottom of FIG. 5. In this example, the proximal end can also include, as shown, the liquid flow carrying the fill members 7 within the catheter 5 and within a pump cylinder 9. A pump plunger 10 is shown in FIG. 5 as being extended, such as before the flow of the fill members 7 through the catheter 5 and into the net or mesh enclosure 2.

Figure 6:
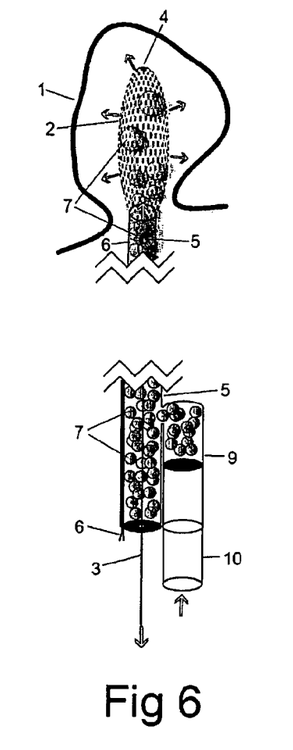

FIG. 6 continues to show this example of the proximal end of the catheter 5, corresponding to the example of the configuration of the distal end shown in FIG. 2. In the example of FIG. 6, the elongated member 3 has been detached from the location 4 on the net or mesh enclosure 2, and the elongated member 3 has been drawn outward, such as through a liquid-tight opening in the proximal end of the catheter 5. Also in the example of FIG. 6, the pump plunger 10 has been partially compressed into the pump cylinder 9, such as for starting or inducing a liquid flow carrying the fill members 7 through the catheter 5 into the net or mesh enclosure 2. The liquid (e.g., sterile saline) flow carrying the fill members 7 can be self-contained within the pump cylinder 9, in an example, or can be introduced into the pump cylinder 9 from an external reservoir that can be connected via a luer lock, a one-directional valve, and a tube. As shown in the upper portion of FIG. 6, and also in FIG. 2, the liquid portion of this flow can escape through the net or mesh enclosure 2, while the fill members 7 are retained in the net or mesh enclosure 2, thereby causing the net or mesh enclosure 2 to gently expand.

Figure 7:
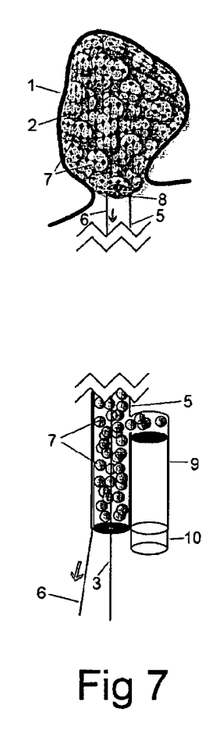

FIG. 7 continues to show this example of the proximal end of the catheter 5, corresponding to the example of the configuration of the distal end shown in FIG. 3. In the example of FIG. 7, the pump plunger 10 has been compressed enough into the pump cylinder 9 to completely fill and expand the net or mesh enclosure 2 with the fill members 7. Also in the example of FIG. 7, the cord or cord-like closure 6 can be pulled away from proximal end of the catheter 5. This can cause the elastic closure ring 8 portion of the closure 6 to close and detach from the distal end of the catheter 5. This keeps the fill members 7 within the net or mesh enclosure 2, and allows withdrawal of the catheter 5 from the net or mesh enclosure 2.

Figure 8:
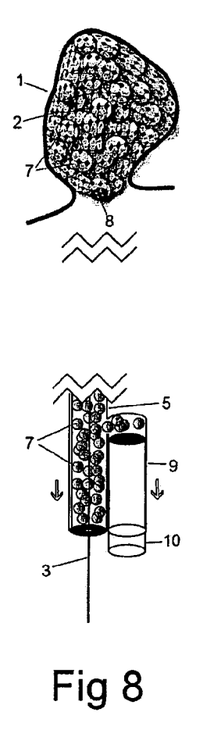

FIG. 8 continues to show this example of the proximal end of the catheter 5, corresponding to the example of the configuration of the distal end shown in FIG. 4. In the example of FIG. 8, the catheter 5 can be removed from the body, leaving behind the closed net or mesh enclosure 2, filled with the fill members 7, expanded, and gently engaged with the walls of the aneurysm 1, thereby inhibiting or preventing prolapse into the parent vessel. These devices, methods, and techniques can provide relatively rapid and thorough occlusion of the aneurysm 1.

Figure 9:
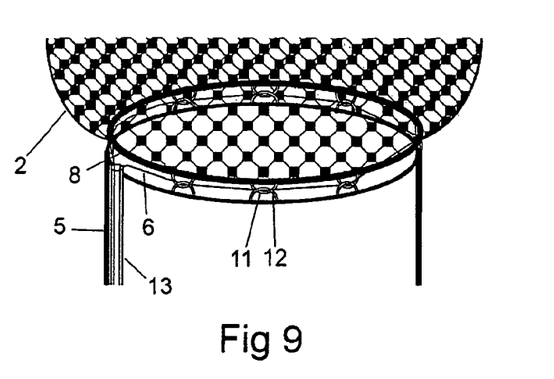
FIG. 9 and FIG. 10 show a detailed view of an example of a closure mechanism for the net or mesh enclosure. In this example, the closure mechanism can include an elastic ring and a removable attachment cord.
Figure 10:
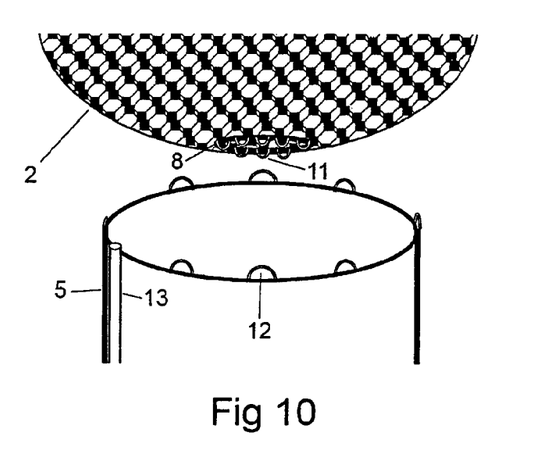

FIGS. 9-10 show a detailed view of an example of how the net or mesh enclosure 2 can be closed and then detached from the catheter 5. This detailed view of FIGS. 9-10 can correspond to the larger-scale views of the cord or cord-like closure 6 and the closure ring 8 shown in FIGS. 3 and 7. In this example shown in FIGS. 9-10, there can be an elastic closure ring 8, forming an opening at the proximal portion of the net or mesh enclosure 2, that can be attached to the catheter 5, such as by the connection of the loops 11 on the closure ring 8, and loops 12 on the catheter 5. These loops 11 and 12 can be temporarily coupled or connected to each other, such as by the cord or cord-like closure 6. The cord or cord-like closure 6 can travel to this area through a small lumen 13 that can extend through the length of the catheter 5.

In the example of FIG. 9, the cord or cord-like closure 6 can thread through the loops 11 on the elastic closure ring 8 and also through the loops 12 on the catheter 5, thereby coupling or connecting respective loops 11 and 12 together. This connection can hold the elastic closure ring 8 open and in connection with the catheter 5. In the example of FIG. 10, after the net or mesh enclosure 2 has been filled, the cord or cord-like closure 6 can be pulled away, thereby detaching the loops 11 from the loops 12, thereby allowing the elastic closure ring 8 to close, and also detaching the net or mesh enclosure 2 from the catheter 5.

In an example, the aneurysm occlusion device can be pre-packaged as a kit, such as in a sterile enclosure that includes various components (e.g., the net or mesh enclosure 2, the fill members 7, the catheter 5, the guidewire or other elongated member 3, or any ancillary components). In an example, different kits can be provided. The components included in a particular kit can be pre-selected, such as for the purpose toward which that particular kit is directed, which can be based on one or more patient-specific or other criteria. For example, aneurysms can range in size. Aneurysms sized between 3 mm and 3 cm are believed to be good targets for treatment by an aneurysm-filling occlusion device, such as described herein, and other aneurysm sizes may also be acceptable targets. In an example, various kits are provided for various corresponding aneurysm sizes (e.g., 3 mm, 5 mm, 7 mm, 1 cm, 1.5 cm, 1.75 cm, 2.0 cm, 2.25 cm, 2.5 cm, 2.75 cm, 3.0 cm, or physical sizes that can be expressed as a percentage of or normalized to a particular aneurysm size, e.g., percent of a 1 cm aneurysm, or the like). The components within a particular kit can be pre-selected to be most suitable for a particular sized aneurysm. For example, a kit directed toward a smaller aneurysm can include a smaller net or mesh enclosure 2, smaller-sized fill members 7, or the like. The components (e.g., the net or mesh enclosure 2 or the fill members 7) can be specified in terms of their actual physical size measurements, in an example, or in terms of a percentage of or normalized to a particular component size. A kit directed toward a larger aneurysm can include a larger net or mesh enclosure 2, larger-sized fill members 7, or the like.

In addition or as an alternative to differentiation based on aneurysm size, kits can be differentiated from each other using one or more other parameters, such as aneurysm morphology, aneurysm location (e.g., anterior, posterior, middle cerebral artery, basilar artery, etc.), location of rupture-vulnerable portion or distension within the aneurysm, or any other parameter, such as a patient-directed parameter, or a clinical-procedure-directed parameter (e.g., imaging modality to be used during the procedure, etc.).

Although the fill members 7 have been illustrated as generally uniform in size, this is not required. In addition to the above example in which different kits include differently-sized fill members 7, the same kit can include differently-sized fill members 7, such as for introducing differently-sized fill members 7 into the same net or mesh enclosure 2 for occluding an aneurysm. It can be advantageous to introduce two or more different sizes of fill members 7 into the same net or mesh enclosure 2 for occluding a particular aneurysm.

As an illustrative example, consider a case in which the fill members 7 include small balls and large balls. If the relative sizes are such that the small balls can pass through interstices between the large balls after the large balls have been packed into the net or mesh enclosure 2, then it may be advantageous to first fill the net or mesh enclosure 2 with the large balls, then continue filling the net or mesh enclosure 2 with the small balls. In another example, it may be advantageous to first introduce the small balls into the net or mesh enclosure 2, such as to take up positions closer to the aneurysm wall, then introduce the large balls into the net or mesh enclosure 2. This can help enhance the conformal fit between the aneurysm occlusion device and the walls of the aneurysm, for example, if there is a small nipple or other distension extending from the main portion of the aneurysm sack. In another example, this can help the aneurysm occlusion device adjust to any post-treatment morphological changes to the aneurysm. In an example, the aneurysm occlusion device or its delivery system can be configured to allow a user to select which size balls are being introduced first, or to controllably actuate the delivery of small balls, the delivery of large balls, or to switch between delivering the small balls and delivering the large balls, such as in response to a user command or action. In an example, this can be accomplished by providing different pump cylinders 9 for loading differently-sized fill members 7. For example, the small balls can be loaded from a first pump cylinder 9, and the large balls can be loaded from a different second pump cylinder 9, which can be separately actuated by the user. Not only can the fill members 7 have different sizes, in an example, they can additionally or alternatively have different softnesses, and delivery of the different softness fill members 7 can be user-actuatable, such as by providing separate pump cylinders 9 such as described above.

In another example, the net or mesh enclosure 2 need not be of uniform tensile strength, flexibility, plasticity, or elasticity. For example, some aneurysms can have one or more portions that are more vulnerable to rupture than other portions. In an example, the net or mesh enclosure can be made stronger at or near one or more locations that will be positioned at or near such vulnerable portions of the aneurysm, and less strong but more flexible at one or more other locations that will not be posited at or near such vulnerable portions of the aneurysm. As an illustrative example, if it is known to the clinician that a distal portion of a spherical aneurysm is vulnerable to rupture, then a net or mesh enclosure 2 can be provided, in which the top (e.g., distal) one-third of the net or mesh enclosure 2 is stronger than the bottom (e.g., proximal) two-thirds of the net or mesh enclosure 2. In this example, such as where there is a trade-off between strength and flexibility, the bottom two-thirds of the net or mesh enclosure can be provided with comparatively greater flexibility, while still providing adequate strength where it is needed most. Such differential strength, differential flexibility, differential plasticity, or differential elasticity of one or more regions of the net or mesh enclosure 2 relative to one or more other regions of the net or mesh enclosure 2 can be used as differentiating characteristic by which different kits can be created, e.g., differentiated by a particularly tailored net or mesh enclosure 2. For example, it is believed that aneurysms located in the middle cerebral artery can possibly benefit from a differential strength characteristic of the net or mesh enclosure 2, while aneurysms located in the basilar artery are believed to be more likely to benefit from a uniform strength net or mesh enclosure 2. In an example, the net or mesh enclosure 2 can be omitted, if so desired by the clinician.

In an example, the fill members 7 can include (e.g., be made of, impregnated with, coated with, etc.) a material that activates or promotes the fill members 7 to clot and adhere to each other upon exposure to cerebrospinal fluid (CSF), but that does not activate or promote clotting or adhering of the fill members 7 to each other in the presence of blood. This can promote safety if the aneurysm should rupture. If a brain aneurysm ruptures, this event will expose the fill members 7 to CSF, which will encourage their clumping together. Such clumping together can help inhibit, reduce, or prevent bleeding or can help inhibit, reduce, or prevent migration of the fill members 7 away from the location of the ruptured aneurysm. Illustrative examples of materials that activate or promote clotting upon exposure to CSF, but not blood, can include fibrinogen or prothombin, which can be incorporated into the fill members 7.

In an example, all or selected portions of the aneurysm occlusion device described herein can be configured to be introduced under use of one or more imaging modalities to help proper placement, such as radiographic imaging (e.g., computed tomography (CT) scanner, fluoroscope, four-vessel cerebral angiography, etc.), magnetic resonance (MR) imaging (MRI), ultrasound imaging, or other imaging modality. In an example, the fill members 7 can be configured to be radio-opaque, such that they are visible using a radiographic imaging modality, and the net or mesh enclosure 2 can be configured to be radiolucent, such that it is not visible using a radiographic imaging modality (e.g., so that the underlying fill members 7 can be observed using the radiographic imaging modality). In this example, the net or mesh enclosure 2 can be configured to be echogenic, such that it is observable using an ultrasound imaging modality, or MR-compatible and MR-visualizable, such that it is observable using an MR imaging modality.

Additional Notes

The above detailed description includes references to the accompanying drawings, which form a part of the detailed description. The drawings show, by way of illustration, specific embodiments in which the invention can be practiced. These embodiments are also referred to herein as "examples."

Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

We claim:

1. A device to treat an aneurysm comprising:
a plurality of individual soft and compressible non-liquid fill members;
a flow conduit, providing a liquid flow that carries the individual, non-liquid fill members using the liquid flow;
a flexible, expandable, and liquid-permeable net or mesh enclosure, configured to be inserted into and to fit within the aneurysm, wherein the net or mesh enclosure comprises a primary opening that is configured to receive the plurality of individual, non-liquid fill members into the net or mesh enclosure and wherein the primary opening is closable after the plurality of individual, non-liquid fill members have been received into the net or mesh enclosure; and wherein the net or mesh enclosure further comprises a plurality of secondary openings that allow the liquid flow that carried the individual, non-liquid fill members into the net or mesh enclosure to pass through the net or mesh enclosure but retain the plurality of individual, non-liquid fill members within the net or mesh enclosure, wherein a resulting accumulation of the plurality of individual, non-liquid fill members within the net or mesh enclosure causes the net or mesh enclosure to expand and to come into contact with the aneurysm walls to thereby substantially occlude the aneurysm and retain the net or mesh enclosure within the aneurysm, wherein at least some of the non-liquid fill members retained by the net or mesh enclosure partially protrude out from the net or mesh enclosure to assist in conformal gripping of the interior aneurysm wall; wherein a proximal region of the net or mesh enclosure has a first strength, flexibility, plasticity, or elasticity; wherein a distal region of the net or mesh enclosure has a second strength, flexibility, plasticity, or elasticity; wherein there is a difference between the first strength, flexibility, plasticity, or elasticity and the second strength, flexibility, plasticity, or elasticity; and
a user-actuatable closure, associated with the primary opening in the net or mesh enclosure through which the individual non-liquid fill members are introduced into the enclosure, wherein the closure is configured to be user-actuated to reduce a size of the primary opening after the net or mesh enclosure has been expanded by filling it with the fill members.

2. The device of claim 1, wherein the plurality of individual, non-liquid fill members are non-inflammatory, implantably non-biodegradable, and anti-bacterial or anti-microbial, and at least one of the individual, non-liquid fill members comprises at least one of a sponge material, a foam material, or a gel material.

3. The device of claim 1, wherein at least one of the individual, non-liquid fill members is configured to be shaped as at least one of a sphere, an ovoid, an ellipsoid, or a polyhedron.

4. The device of claim 1, wherein the individual, non-liquid fill members include a Shore OO value within a range of about 5 to about 50.

5. The device of claim 1, wherein the individual, non-liquid fill members include a size within a range of about 50 micrometers to about 2000 micrometers.

6. The device of claim 1, wherein the plurality of individual, non-liquid fill members includes fill members of different sizes.

7. The device of claim 1, wherein the individual, non-liquid fill members include a material causing more adhesion of the individual, non-liquid fill members to each other in the presence of cerebrospinal fluid (CSF) than in the presence of blood.

8. The device of claim 1, wherein the individual, non-liquid fill members are radio-opaque.

9. The device of claim 1, wherein the net or mesh enclosure comprises at least one of a nylon material, a polypropylene material, a polyester material, or a polytetrafluorethylene material, or a polytetrafluoroethene material.

10. The device of claim 1, wherein the net or mesh enclosure is initially folded or compressed for insertion into the aneurysm.

11. The device of claim 1, wherein the net or mesh enclosure is radiolucent.

12. The device of claim 1, wherein the net or mesh enclosure is echogenic.

13. The device of claim 1, wherein the net or mesh enclosure is MR-visible.

14. The device of claim 1, wherein the net or mesh enclosure is configured with at least one of a differential strength, differential flexibility, differential plasticity, or differential elasticity between different regions of the net or mesh enclosure.

15. The device of claim 1, further comprising an elongated flexible intravascular member sized and shaped for intravascularly transporting the individual, non-liquid fill members and the net or mesh enclosure into the aneurysm.

16. The device of claim 15, wherein the elongated flexible intravascular member comprises a catheter comprising the conduit.

17. The device of claim 16, wherein the net or mesh enclosure comprises the primary opening configured to be drawn shut using a closure that is detachable from the elongated flexible intravascular member or detachable from an instrument or mechanism associated with the elongated flexible intravascular member.

18. The device of claim 16, wherein the closure comprises at least one of a cord, a wire, a tie-off, a threaded member, a shape-memory material, a clasp, an adhesive, or a fusion.

19. The device of claim 15, comprising an elongated member configured to extend outward from the elongated flexible intravascular member into the aneurysm within the net or mesh enclosure to push the net or mesh enclosure into the aneurysm.

20. A device to treat an aneurysm comprising:
a plurality of individual non-liquid fill members;
a liquid flow which transports the plurality of individual non-liquid fill members;
a flow conduit through which the liquid flow moves and through which the individual non-liquid fill members move, wherein this flow conduit is configured to transport the plurality of non-liquid fill members into an aneurysm;
a pump mechanism that is configured to cause the liquid flow and the plurality of individual non-liquid fill members to move through the flow conduit into the aneurysm;
a flexible and liquid-permeable net or mesh enclosure that is configured to be inserted into the aneurysm; wherein the net or mesh enclosure comprises a primary opening that is configured to receive the plurality of individual non-liquid fill members into the net or mesh enclosure and wherein the primary opening is closable after a plurality of non-liquid fill members have been received into the net or mesh enclosure; wherein the net or mesh enclosure further comprises a plurality of secondary openings that allow the liquid flow to pass outwards through the net or mesh enclosure but to retain the plurality of individual non-liquid fill members within the net or mesh enclosure; wherein a resulting accumulation of the plurality of individual non-liquid fill members within the net or mesh enclosure causes the net or mesh enclosure to expand and to come into contact with the aneurysm walls to thereby substantially occlude the aneurysm; and wherein at least some of the non-liquid fill members retained by the net or mesh enclosure partially protrude out from the net or mesh enclosure to assist in conformal gripping of the interior aneurysm wall; and
a closure associated with the primary opening in the net or mesh enclosure through which the individual non-liquid fill members enter the enclosure, wherein user actuated closing of this closure prevents the individual non-liquid fill members from escaping outwards from the net or mesh enclosure through this primary opening.

21. A method comprising:
creating a flexible, expandable, and liquid-permeable net or mesh enclosure to occlude an aneurysm wherein a proximal region of the net or mesh enclosure has a first flexibility or elasticity; a distal region of the net or mesh enclosure has a second flexibility or elasticity; and the first flexibility or elasticity is different than the second flexibility or elasticity;
inserting the flexible, expandable, and liquid-permeable net or mesh enclosure into an aneurysm;
providing a liquid flow that introduces a plurality of soft and compressible individual, non-liquid fill members, using a flow conduit, into the net or mesh enclosure;
receiving the individual, non-liquid fill members into the net or mesh enclosure through a primary opening in the net or mesh enclosure;
retaining the individual, non-liquid fill members within the net or mesh enclosure while allowing liquid flow that carried the individual, non-liquid fill members into the net or mesh enclosure to pass through a plurality of secondary openings in the net or mesh enclosure such that a resulting accumulation of the plurality of individual, non-liquid fill members within the net or mesh enclosure causes the net or mesh enclosure to expand and to come into contact with and generally conform with an interior wall of the aneurysm to thereby substantially occlude the aneurysm and retain the net or mesh enclosure within the aneurysm;
allowing at least some of the retained non-liquid fill members to partially protrude out from the net or mesh enclosure to assist in conformal gripping of an interior wall of the aneurysm; and
actuating a closure to reduce the size of the primary opening, though which individual, non-liquid fill members were introduced into the net or mesh enclosure, after the net or mesh enclosure has been expanded.

22. The method of claim 21, wherein inserting the net or mesh enclosure into the aneurysm comprises inserting an initially folded or compressed net or mesh enclosure into the aneurysm.

23. The method of claim 21, comprising intravascularly guiding a distal portion of an elongated flexible member to an aneurysm for inserting the net or mesh enclosure into the aneurysm, for introducing the individual, non-liquid fill members into the net or mesh enclosure, and for accumulating enough of the individual, non-liquid fill members within the net or mesh enclosure to expand the net or mesh enclosure.

24. The method of claim 23, comprising detaching the net or mesh enclosure from the elongated flexible member after expanding the net or mesh enclosure to substantially fill the aneurysm.

25. The method of claim 24, comprising drawing shut the primary opening of the net or mesh enclosure before detaching the net or mesh enclosure from the elongated flexible member.

26. The method of claim 21, wherein introducing a plurality of soft and compressible fill members, using a liquid flow, into the net or mesh enclosure comprises introducing at least two different sizes of individual, non-liquid fill members.

27. The method of claim 26, wherein the introducing at least two different sizes of individual, non-liquid fill members is carried out in response to user-actuation controlling which size of individual, non-liquid fill member is to be introduced.

28. The method of claim 21, comprising self-adhering the individual, non-liquid fill members to each other upon exposure to cerebrospinal fluid.

29. The method of claim 21, comprising using a net or mesh enclosure 26 having at least one of a differential strength, differential flexibility, differential plasticity, or differential elasticity between different regions of the net or mesh enclosure.

30. The method of claim 21, comprising viewing the individual, non-liquid fill members using a first imaging modality and viewing the net or mesh enclosure using a different second imaging modality.

* * * * *